United States Patent [19]

Jannone

[11] 4,295,368

[45] Oct. 20, 1981

[54] METHOD FOR MEASURING THE FULL RANGE IN QUALITY OF A VAPOR

[76] Inventor: Joseph Jannone, 133-48 84th St., Ozone Park, New York, N.Y. 11417

[21] Appl. No.: 68,686

[22] Filed: Aug. 22, 1979

[51] Int. Cl.³ ............................................ G01K 17/00
[52] U.S. Cl. ...................................... 73/192; 73/61.3
[58] Field of Search ................... 73/192, 61.3, 190 R, 73/204

[56] References Cited

U.S. PATENT DOCUMENTS

| | | | |
|---|---|---|---|
| 898,610 | 9/1908 | Thomas | 73/192 |
| 946,886 | 1/1910 | Thomas | 73/204 |
| 2,456,163 | 12/1948 | Watson | 73/23 |
| 3,363,460 | 1/1968 | Baumann | 73/192 |
| 3,413,838 | 12/1968 | Duddy | 73/61.3 X |
| 3,429,186 | 2/1969 | Price et al. | 73/421.5 R |
| 3,479,872 | 11/1969 | Tauson | 73/192 |
| 3,950,136 | 4/1976 | Bellings | 73/421.5 X |

FOREIGN PATENT DOCUMENTS 2263754  12/1972  Fed. Rep. of Germany ........ 73/192

OTHER PUBLICATIONS

Publ. "Thermodynamics of Engineering Science", S. L. Soo; 1958, pp. 120-123.

Primary Examiner—Daniel M. Yasich

[57] ABSTRACT

A method for determining the quality of a vapor wherein a representative sample is heated at constant volume to a superheated or compressedliquid state so that a measurement of the pressure and temperature in this state, in addition to knowing the pressure or temperature of the vapor, will uniquely determine the vapor quality by means of an appropriate relationship. The method is not limited to the degree of wetness and does not require calibration.

1 Claim, 3 Drawing Figures

METHOD FOR MEASURING THE FULL RANGE IN QUALITY OF A VAPOR

This invention relates, generally, to an apparatus and method of calorimetry and more particularly to an apparatus and method for measuring the full range in quality of a vapor.

In a more specific aspect, the present invention relates to a method of calorimetry which utilizes a fixed volume sampling chamber to simply and accurately determine the vapor quality of any substance, irrespective of its degree of wetness.

The wetness or wetness fraction may be defined as the percentage by weight of the substance in the wet saturated condition in a given sample. Several methods of wetness fraction measurement have been devised of varying accuracy, complexity, and applicability. The selection of an appropriate method with present day technology depends on the accessibility of the wet fluid flow and particularly on the form of the liquid phase; i.e., coarse liquid or fog. The available methods will be reviewed according to their application and note made of their limitations and any existing problems.

When the wetness fraction of the fluid is high it will have large liquid drops (>10 μm diameter) within the flow. Here, mechanical separation methods are therefore feasible and have been used fairly successfully. In addition to mechanical separation, tracer methods have also been used where a known mass flow rate of a solution of an easily detectable trace element is introduced into the main wet fluid stream. The concentration of this element before and after injection is measured and the wetness fraction is then determined by an appropriate correlation. The basic problems with this method is that adequate mixing is essential and the concentration after mixing is usually very small and difficult to measure. Both these factors tend to reduce the accuracy of this method. All of the above methods have a severe limitation in that they fail to properly measure the wetness fraction when it has a low value.

When the wetness fraction is low many devices have been proposed which generally may be grouped into two categories: methods requiring calibration and direct or absolute methods. According to the known calibration methods, several features of the flow such as droplet size, size spectrum and velocity need be determined and hence elaborate calibration may be necessary. The production of flows with particular compositions is extremely difficult, making calibration a major problem. Over a limited range of applications a calibration may be possible. The absorption and dielectric methods are two examples.

In the direct or absolute methods, several schemes have met success, but not without some degree of limitation and problems. A fairly well known method is the throttling method where problems arise from heat loss and incomplete mixing following expansion. Adequate insulation and sufficient sample size can reduce heat loss errors to acceptable proportions however the attainment of thermodynamic equilibrium is more difficult. In addition, this technique has a very small limit of application. Other methods which have been employed include heating, condensing and psychrometric methods. When the fluid to be measured is under vacuum, a probable error analysis reveals that the heating method offers the least amount of erroneous measurements. The throttling method does not sample fluids under vacuum. Thus, limited accuracy and applicability is present with all the above methods.

More recently, techniques utilizing light-scattering probes have been developed for wetness fraction measurements. These techniques however are quite complex and require a computer program to calculate the approximate calibration curve needed, including the optical particularities. Different probe types are needed for different applications and problems do exist in calibration. In low pressure applications, such as in steam turbines, the droplets are so small that they need a small scattering volume to keep coincidence errors low. Additionally, because of the high flow speeds, the duration of the droplets in the scattering volume are extremely small that the instruments reach their limits of capacity and therefore have a limited application. Since this is an electronics-time problem, further optical (special apertures) modifications can be applied to increase the "resolution" time. This, however, will only add to the complexity of the system and involve further corrections for optical errors.

In high pressure applications, such as wet steam supply in light-water nuclear power plants, a different probe type must be used. Here, the small amount of wetness at the turbine inlet is not only important for the determination of the turbine efficiency, but can also cause erosion of the steam pipe and high pressure blading in some cases. Difficulties arise mainly from thermodynamic considerations, namely the pressure and temperature of the steam creates severe forces on the instrument in addition to sealing, optical and otherwise, corrosion, and thermal stress problems.

The present invention, therefore, has the principal object of providing a universal method and apparatus for determining the quality or wetness fraction of any substance by utilizing a fixed volume container to capture a representative sample of the substance, heating said sample to a superheated or compressed liquid state and measuring the pressure and temperature thereof, whereby the quality (or wetness fraction) is uniquely determined by using the well known quality-specific volume relationship.

Another object of the invention is to provide a method for obtaining a representative sample without expanding the vapor to atmospheric or other lower than system pressure.

Still another object of the invention is to provide a simple and accurate method of determining the quality or wetness fraction of a liquid vapor covering the entire vapor region.

Additional objects and advantages of the present invention will become apparent from a reading of the specification taken in conjunction with the accompanying drawing in which.

Broadly contemplated, the present invention provides an apparatus for determining the quality of a fluid vapor comprising flow means for flowing wet vapor in a closed atmosphere, an open sampling chamber, means for having a portion of said vapor flowing through said flow means flow through said sampling chamber at substantially the same pressure and temperature as said vapor flowing through said flow means, means for sealing said sampling chamber for sealing a representative portion of wet vapor therein, heating means for heating said vapor sealed in said chamber and being adapted to increase the pressure and temperature thereof until in a region of superheat or liquid and means for removing heat from said sampling chamber.

In another broad aspect, the present invention provides a method for determining and qualifying the quality of a fluid vapor comprising the steps of (1) providing a source of fluid vapor, (2) directing a portion of said vapor through an open sampling chamber at substantially the same pressure and temperature as the vapor existing in said souce, (3) sealing said chamber to seal a representative portion of vapor therein, (4) applying heat to said captured vapor to change the state of said vapor to a superheated or liquid condition, (5) substantially removing heat to said captured vapor so as to establish a cooling mode for said superheated vapor or liquid, and (6) observing the pressure and temperature in said closed sampling chamber during said cooling mode, whereby the quality of said vapor source is determined by correlating the determinable specific volume of the superheated vapor or liquid to the conditions of said source, wherein said determined quality is qualified by observing the equality of the determinable specific volumes during said cooling mode.

Figure 1:
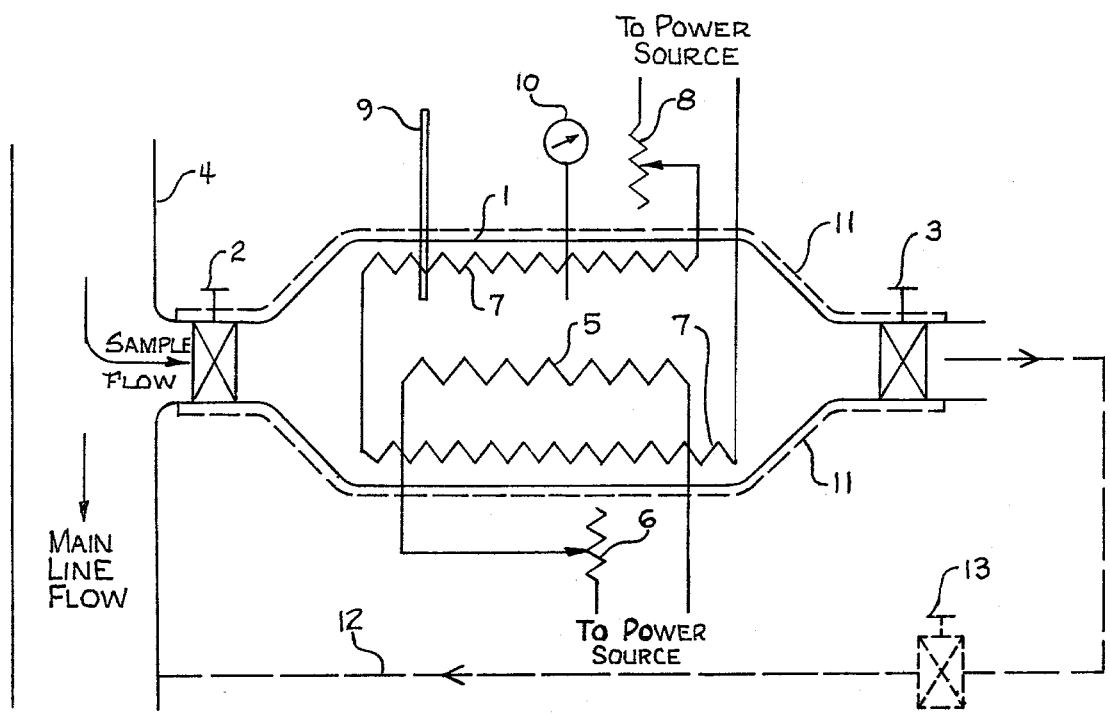
FIG. 1 is a diagrammatic view of a calorimeter system embodying principal features of the invention.

Referring particularly to FIG. 1, it will be seen that the apparatus comprises a sampling chamber generally represented by reference numeral 1. Inlet valve 2 and exit valve 3 are adapted to permit passthrough of vapor through the chamber or to seal vapor within the chamber. Heat may be applied to the chamber by electrical resistance element 5, adjustable resistor 6 and a power source (not shown). Alternatively and preferably an electrical heating element 7 is disposed circumferentially and in close proximity to the wall of chamber 1 and is in communication with adjustable resistor 8. A temperature sensing device such as thermocouple 9, and a pressure sensing device such as pressure gage 10, are positioned for appropriate temperature and pressure readings. Surrounding the apparatus is an insulating material 11 which provides heat transfer protection. A pressure regulating valve 13 is also provided for regulating pressure.

Figure 2:
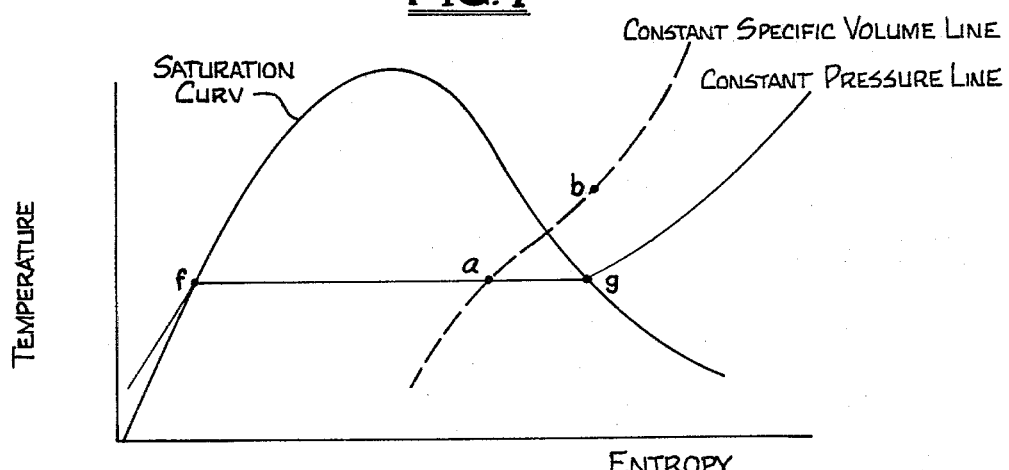
FIG. 2 is a graphic view showing a constant specific volume line on a typical temperature versus entropy diagram.
Figure 3:
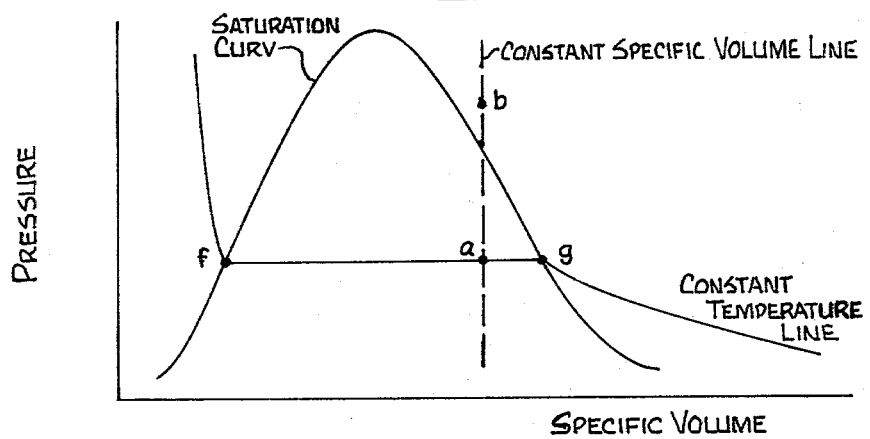
FIG. 3 is a graphic view showing a constant specific volume line on a typical pressure versus specific volume diagram.

In a typical technique of operation and with reference to the drawing, consider an arbitrary constant specific volume line as shown in FIGS. 2 and 3 by the dash line. Now also referring to FIG. 1, a representative vapor sample which enters the chamber 1 via the inlet valve 2 and having specific properties may be indicated on the property diagrams as lying at point a. Initially the exit valve 3 and inlet valve 2 are both open to allow a continuous sampling to pass through the apparatus. It is important at this stage to maintain the same condition of the fluid through the apparatus as it existed prior to being sampled, so that the chamber 1 must be guarded against heat transfer and pressure changes. Heat transfer protection can easily be accomplished by thermally insulating the apparatus by any appropriate means, such as an insulating material 11 covering the apparatus. Appreciable pressure changes can be avoided by redirecting the sample flow after leaving the apparatus via the exit valve 3 to some point downstream in the main line 4 where the pressure is fractionally lower (this is indicated by the dash line 12 in FIG. 1), or to any still lower pressure point in the line where now the pressure reduction in the apparatus is limited to a fractional value of the line pressure by means of a pressure regulating valve 13 or any other appropriate device. When this return is not deemed practical, whether for mechanical reasons or the distortion of the two-phase flow being measured, the flow can be vented, and pressure regulated, to the surroundings when the supply pressure is above local ambient pressure. When the supply pressure is below the local ambient pressure, then venting can be accomplished by means of, but not limited to, an auxiliary suction (not shown) where such pressure is controllable to within close limits of the supply pressure. In any case, the slightly lower pressure will allow flow to be established through the apparatus while insignificantly changing the fluids pressure state. For all practical purposes, then, the state indicated by point "a" in FIGS. 2 and 3 is the same as that existing in the main line 4. It should be understood that the main line 4 could also be representative of the location or condition of the fluid to be sampled from whatever source, and hence should not be considered limited to only a main line.

After equilibrium of the flow is established in the apparatus, the inlet and exit valves 2, 3 are closed in a manner allowing a representative sample to be entrapped within the sampling chamber 1. The valving should be of such type that, once closed, it will maintain the chamber 1 in a hermetically sealed condition. Heat is then applied to the entrapped sample by any appropriate means. One means is shown in FIG. 1 and comprises an electrical resistance heating element 5, an adjustable resistor 6, and a power source (not shown). Heating is maintained until the fluid becomes dry and enters into its superheated state. This heat addition process will then be one of constant volume so that we may represent this condition as point b on the property diagrams; i.e., point b lies on the same constant specific volume line passing through point a.

An alternate and preferred means of heating is to have either the wall of the sampling chamber 1 function as the heating element by use of appropriate material or an electrical resistance heating element 7 displaced circumferentially and in close proximity to the wall of said chamber. Said heating element is in communication with an adjustable resistor 8, also shown in FIG. 1. This arrangement has the advantage of maintaining the wall of the chamber in closer thermal equilibrium with the sample fluid during the measuring phase, especially if the insulation should become ineffective.

In order to avoid some possible thermodynamic and measurement problems which could occur during the heating phase, the current is turned off to the heating element by means of the adjustable resistor 6 (or 8) or set to a very low value after a superheated condition is achieved. This will cause the heating element to quickly cool to, or in close proximity of, the temperature of its surroundings and thus avoid any influence of thermal radiation and/or conduction that the element may have on the temperature measuring sensor. The dry sample will now start to cool by heat transfer to the surroundings of the apparatus, but this should occur fairly slowly since the insulation will prevent any rapid heat loss. This therefore allows reading the temperatures by means of a temperature sensing device 9, and pressure by means of a pressure sensing device 10, over a reasonable length of time without any significant change in the sample properties. At the same time, this will allow the instruments to have some time lag as most instruments in general possess this characteristic. Most importantly, since the cooling mode will be a relatively slow process, this allows the sample to cool uniformly so that any temperature and pressure measurements will be representative of the thermodynamic (macroscopic) state of the sample at any instant in time.

A simple means exists for qualifying ay measurement taken. By obtaining a series of measurements of pressure and temperature of the sample during the cooling mode, a constant specific volume line should be produced with this data when the system is operating properly and there are no errors in the measurements. Obviously, then, the reliability of any data can be checked by this simple method.

By knowing the pressure or temperature in the main line, the wetness fraction (or quality) is then determined directly from an appropriate relationship of the specific volumes and wetness fraction (or quality):

$$v_a = v_b = v_g - w(v_g - v_f)$$

or $$v_a = v_b = v_f + x(v_g - v_f).$$

In the above relationships, $v_a$ and $v_b$ are the specific volume of the sample (enclosed volume of the sampling chamber 1 divided by the mass of the entrapped sample) which is determined from the measurements of pressure and temperature of the sample in the superheated or compressed liquid state and a table of thermodynamic properties; $v_g$ is the dry saturated specific volume of the fluid vapor source in the main line; $v_f$ is the wet saturated specific volume of the fluid vapor source in the main line; w is the wetness fraction and x is the quality. Since everything except w or x can be determined in these relations, then w or x is the only unknown and therefore solvable quantity.

The present invention, then, is seen not to be limited to the form of the vapor phase (degree of wetness) since any representative sample can be introduced into the device irrrespective of its wetness fraction and analyzed. In fact, it is capable of correct measurement whether the initial sample pressure is high or low and therefore also not limited to pressure. The only problem which may exist in certain applications is the extraction of a representative sample, which is a problem common to all similar devices.

Accordingly, this invention has the advantages of accuracy, simplicity, reliability, inherently selfqualifying, not requiring calibration, and an unlimited range of application. Other modifications and variations of the present invention as set out herein may be made without departing from the spirit thereof and such modifications are meant to be included in the appended claims.

What is claimed is:

1. A method for determining the quality of a fluid vapor comprising the steps of (1) providing a source of fluid vapor, (2) directing a portion of said fluid vapor through an open insulated sampling chamber at substantially the same pressure and temperature as the fluid vapor in said source, (3) sealing said chamber to seal a representative portion of fluid vapor therein, (4) applying heat to said representative portion of fluid vapor to change the state of said representative portion of fluid vapor to a superheated or liquid condition, (5) cooling said representative portion of fluid vapor to establish a cooling mode for said superheated vapor or liquid wherein the temperatures and pressures during said cooling mode are recorded, (6) utilizing the temperature and pressure readings during said cooling mode while in the superheated state to determine the specific volume of the fluid vapor source; and (7) thereafter determining the quality of said fluid vapor source by the following equation:

$$V_a = V_b = V_f + X(V_g - V_f)$$

wherein $V_a$ and $V_b$ individually is the specific volume of the representative portion;

$V_g$ is the dry saturated specific volume of the fluid vapor source;

$V_f$ is the wet saturated specific volume of the fluid vapor source; and

X is the quality of the fluid vapor source.

* * * * *